(12) United States Patent
Spangle

(10) Patent No.: US 7,765,883 B1
(45) Date of Patent: Aug. 3, 2010

(54) DRY BLENDING AID

(75) Inventor: Lloyd Byron Spangle, Claremore, OK (US)

(73) Assignee: Catalyst Partners, Inc., Chico, TX (US)

( * ) Notice: Subject to any disclaimer, the term of this patent is extended or adjusted under 35 U.S.C. 154(b) by 93 days.

(21) Appl. No.: 12/106,545

(22) Filed: Apr. 21, 2008

Related U.S. Application Data

(60) Provisional application No. 60/916,648, filed on May 8, 2007.

(51) Int. Cl.
  *G01N 33/00* (2006.01)
  *G01N 5/00* (2006.01)
  *G01N 33/38* (2006.01)

(52) U.S. Cl. ....................................................... 73/866

(58) Field of Classification Search .................... 73/866, 73/863.23; 800/306
  See application file for complete search history.

(56) References Cited

U.S. PATENT DOCUMENTS

| | | | |
|---|---|---|---|
| 3,565,533 A * | 2/1971 | Garcia et al. .............. 73/866 X |
| 3,565,553 A | 2/1971 | Rinehart et al. |
| 3,615,223 A | 10/1971 | Burroughs et al. |
| 4,003,431 A | 1/1977 | Novotny et al. |
| 4,654,165 A | 3/1987 | Eisenberg |
| 5,324,356 A | 6/1994 | Goodwin |
| 5,467,659 A * | 11/1995 | Young .......................... 73/866 |

* cited by examiner

*Primary Examiner*—Thomas P Noland
(74) *Attorney, Agent, or Firm*—William P. Ramey, III

(57) ABSTRACT

A method of monitoring and evaluating the dry-blending of powders and granular materials via the use of non-dissolvable particulate matter such as mustard seed as a blending aid. The mustard seed is blended into the total batch of dry blend materials and the mustard seed can subsequently be extracted by a process of sieving from a known volume of sample taken of the mixture since the mustard seed is larger than the other particles that are being blended. The weight and or sight count of the extracted mustard seed present in the sample is determined and compared with the amount of seed that should be present in a perfect blend to determine if the dry blend materials are thoroughly mixed.

16 Claims, No Drawings

DRY BLENDING AID

CROSS-REFERENCE TO RELATED APPLICATIONS

The present application claims priority to U.S. Provisional Patent Application for DRY BLENDING AID filed on May 8, 2007 as Application No. 60/916,648.

BACKGROUND OF THE INVENTION

1. Field of the Invention

The present invention is a method that uses a dry blending aid in the form of mustard seeds to monitor and evaluate the dry-blending of powders and granular materials. A known proportion of mustard seed to dry blending materials is added to a mixer and mixed together. Samples are taken, the mustard seeds sieved out of the other materials and measured. The proportion of mustard seeds in the sample are then compared with the expected proportion in the total mixture to determine if the dry blending materials are thoroughly mixed.

2. Description of the Related Art

Currently there is no quick and easy way of directly determining whether dry blending mixtures such as cement are thoroughly blended. Thus the operator must make a determination based on past experience and based on lab results from similar mixtures that were previously mixed.

For example, a sample of dry blended cement mixture is taken from the mixer after a given time interval and taken to the laboratory where it is mixed with water and allowed to harden. The time required for the mixture to harden is an indirect indication of whether the dry blended cement was adequately mixed.

Obviously because of the length of time required to do this type of laboratory work on a sample, in commercial cement mixing operation the mixture upon which the sample was taken will have already been removed from the mixer and new batches will have been mixed. For this reason, this type of testing procedure is not adequate when a new custom blend is being made. In those situations, the blend time needed to thoroughly mix the components might be more or less than the time required for previously tested mixtures having different components.

The present invention addresses this problem by providing a fast and easy way of obtaining a direct measure of the degree of mixing that has occurred in a dry blending mixture. This invention is based on the principal that if one component in the mixture is thoroughly mixed, then all components in the mixture should also be thoroughly mixed. The present invention adds mustard seed as a blending aid in the mixture to be blended. The mustard seed is added at a known concentration to the dry blending mixture and then the mixture is mixed. A sample of the mixture is then obtained and the mustard seeds separated from the other dry mixture components. The mustard seeds are then weighed or counted and the concentration of mustard seeds in the sample is obtained and compared with the theoretical or expected concentration that should be present in the mixture if the mixture is thoroughly mixed. If the concentration of mustard seed in the sample matches the expected concentration, then the mixture is thoroughly mixed. Mustard seeds are inert and non-hazardous and do not affect the properties of the finished mixture. They are therefore a good choice as an indicator of whether the components of the mixture have been adequately mixed.

SUMMARY OF THE INVENTION

The present invention relates to a method of monitoring and evaluating the dry-blending of powders and granular materials via the use of non-dissolvable particulate matter, such as mustard seed, as blending aid. The mustard seed has a unique and uniform size of between 1.5 to 2.0 mm which is larger than the other particles that are being blended, has uniform density, and is inert in that it is not viable seed that will sprout when exposed to moisture. Also, mustard seed is not reactive or hazardous. The mustard seed is blended into the total batch of dry-blend materials and the mustard seed is subsequently extracted from a known sample volume of the mixture by a process of sieving. The weight and or sight count of the extracted mustard seed present in the sample is determined and compared with the amount of seed that should be present in the sample in a perfect blend to determine if the dry blend materials are thoroughly mixed.

DETAILED DESCRIPTION OF THE PREFERRED EMBODIMENT

The present invention relates to a method of monitoring and evaluating the dry-blending of powders and granular materials via the use of non-dissolvable particulate matter, such as mustard seed, as blending aid. The preferred material is mustard seed that has uniform size and is not viable seed. The mustard seed that is used is this method has been processed as would be the case for food grade mustard seed. The seed has a limited variation in size of 1.5 to 2.0 mm. Also, the food grade mustard seeds are not viable and therefore do no sprout when exposed to moisture. Mustard seed is used because it has a unique size and density in an inert structure. This material is blended into the total batch of dry-blend and removed by a process of sieving. Then by weight and or sight count the unique material is extracted and calculated as to amount present verses amount that should be present in a perfect blend.

The amount of blending aid to be added should be 1 to 2 pounds of mustard seed per 1000 pounds of total dry blend. The materials to be blended and the mustard seed blending aid should be added to blender in a manner that is safest for personnel and is recommended by the blender manufacturer. A small amount of the mustard seed blending aid is added directly to the dry-blend materials. It is inert and density compatible with the materials. The blending-aid should be added last after all other materials have been added. There are no known hazards associated with the blending-aid.

At any time during the blending a sample of the dry-blend is extracted (usually about one pound). This can be done at approximately 5 minutes or whatever time is deemed appropriate. An initial sample of the blend should be taken to evaluate the blending and the sample should be obtained by using a dipper that can extract an exact volume from the mixer. The dipper should then be tapped repeatedly to settle the contents. Sufficient excess of the blend should then be added to the dipper to overfill the dipper and then a straight edge can be used to level off the sample at the top of the dipper to obtain an exact and repeatable volume.

The content of the dipper is then used as the sample. The entire sample is dumped into a 20 mesh (0.85 mm to 0.5 mm) screen sieve and sieved through a screen. Although a 20 mesh screen sieve is specified, a 30 mesh screen sieve might also be used, depending on the particle size of the other materials in the sample. The retained particles left on the sieve will be the mustard seed blending aid. These particles are easily separated and identified by this technique. The mustard seed particles can then be weighed and also counted if desired. Of course the material to be dry-blended should be finer than the blending-aid so that they are not retained on the 20 mesh screen or the 30 mesh screen if that screen size is used, with the mustard seed blending aid.

At intervals of 5 minutes or whatever time intervals are deemed appropriate, additional samples can be taken as described for the initial sampling and then those samples can be sieved and the retained particles weighed and also counted if desired.

The results are evaluated and when the amount of measured dry-blending aid found in the sample is consistent with the calculated amount expected for a fully mixed sample of the sample's volume, the blend should be considered homogeneously blended. Blending can be continued further to check for optimum blending time.

An example of the process of the invention would be to add 1 pound of the blending-aid to 1000 pounds of dry material to be blended. This would result in 0.1 gram of blending-aid particles in each 100 grams of blend when a homogeneous blend has been accomplished. If in addition to the evaluation of small admixture blending into a large blend, the determination of the bulk density of the final blend is important, then the use of a ladle or sample dipper of known volume can be used to determine the bulk density of the final product. This is important if the blend mixture includes light weight, density reducing materials such as pozzolans, glass bubbles, or other such materials commonly used in cement mixtures. Bulk density is the weight/volume relationship of a dry material, and is a convenient way to verify accuracy of the blending of large amounts of varying density materials. A verified laboratory small blend is used as the standard to compare field blending samples. A dipper of 1 pint size could be used to extract some material from the blender and the dipper tapped until the volume of the material in the dipper stabilizes. Then excess material added to the dipper to overfill it and then the excess removed with a straight edge to get and exact and repeatable sample size.

The sample should first be weighed and then sieved through a 20 or 30 mesh screen. A large 12 inch sieve that fits the top of a 5 gallon bucket is convenient for this procedure. The retained blending-aid particles left on the screen are then weighed and counted if desired. This will give the weight volume (bulk density) of the entire sample and the weight and count of the blending-aid particles. Since the exact amount of mustard seed blending aid added to the dry-blend is known, the perfect blend amount of mustard seed blending aid is expected to be taken from the extracted sample of dry-blend when blending is complete. If the particles of the same that are retained on the screen are at the calculated concentration for the blend of the blending aid in the batch of materials being blended, then blending is good.

A chart can be created to make it easy for the technician to quickly determine if the amount of mustard seed blending aid contained in a sample falls within the expected range for a fully blended mixture by this particle tracing for blend analysis method. Once created, such a chart is used to verify blending of small concentrations of additive. The particles used have been selected based on their density and size in order to have a traceable particle by simple sieve analysis and visual particle counting. Adding 1 pound of particles to 1000 pounds of blend will result in 0.1 gram of particles in 100 grams of sample if correctly blended. This is approximately 19 particles in a 100 gram sample. A weighed sample of the blend with particles added can be sieved in a large sized sieve of 20 to 30 mesh size. A 12 inch sieve that fits in the top of a 5 gallon bucket is convenient. The particles are easily seen and can be weighed or counted.

Once the mixture is considered to have been well blended, the blend can then be used for the intended purpose since the blending aid is inert and should not interfere with the product.

Alternately, sampling can be continued as long as desired at intervals deemed appropriate to further evaluate the blending procedure. Since the blending-aid is non-reactive it can be added routinely to allow blend checking as desired. The blending-aid of the patent is primarily a dry material blending-aid, but it would be feasible to use the blending-aid in a thick liquid or "slurry" to evaluate mixture efficiency.

Also, it would be feasible to gain information using the blending-aid material of the patent by extracting the blending-aid material in an automated process.

This method was initially designed to enable operators of dry-blending facilities to verify the accuracy of critical dry blends of cement and additives which may be less than 0.1% of the total blend. The method allows the user to evaluate the efficiency of conventional dry-blending facilities when dry powders such as Portland cement and add mixtures are to be blended together in critical mixtures. Also, the method can be utilized for other materials that are not easily evaluated when dry-blended together.

Although the main purpose for this method is cement dry-blending, it can be utilized in other dry-blending operations since the mustard seeds are non-toxic and non-hazardous. Also, as a residue, the mustard seeds are environmentally clean. The method does not present any environmental problems due to toxicity or waste control.

There are no highly technical requirements for the use of the mustard seed blending aid, and the method does not require investment in expensive and fragile monitoring and sensing devices. The method does not require any sophisticated monitoring devices or reactive tracer elements that might contaminate the blend. The mustard seeds are relatively inert in the final mixed product.

While the invention has been described as employing mustard seed, other natural or artificial seeds or grains of similar size and density may optionally be employed instead of the mustard seed.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

What is claimed is:

1. A method of monitoring and evaluating the dry-blending of powders and granular materials comprising:
   a. adding a known amount of non-dissolvable particulate matter to a known amount of materials that are to be blend in a mixture,
   b. blending the mixture for a time interval,
   c. taking a known amount of sample from the mixture,
   d. separating the particulate matter from the other materials in the sample,
   e. determining the amount of particulate matter in the sample either by weighing the particulate matter or counting the particulate matter, and
   f. comparing the actual amount of particulate matter found in the sample verses the expected amount of particulate matter in a completely mixed blend to determine whether the mixture is completely mixed.

2. A method of monitoring and evaluating the dry-blending of powders and granular materials according to claim 1 further comprising:
   g. repeating steps b-f until the determined amount of particulate matter in the sample is the same as the expected amount of particulate matter in a completely mixed blend which indicates that the mixture is completely mixed.

3. A method of monitoring and evaluating the dry-blending of powders and granular materials according to claim 1 wherein the particulate matter is separated from the other materials in the sample by sieving the particulate matter through a mesh screen sieve.

4. A method of monitoring and evaluating the dry-blending of powders and granular materials according to claim 3 wherein the wire mesh screen is selected from the following list:
   20 mesh screen sieve and 30 mesh screen sieve.

5. A method of monitoring and evaluating the dry-blending of powders and granular materials according to claim 1 wherein the sample is weighted before the particulate matter is separated from the sample and the particulate matter is weighed after it is separated from the sample to determine the amount of particulate matter in the sample.

6. A method of monitoring and evaluating the dry-blending of powders and granular materials according to claim 1 wherein a known volume of sample is used and the particulate matter that is separated from the sample is counted to determine the amount of particulate matter in the sample.

7. A method of monitoring and evaluating the dry-blending of powders and granular materials according to claim 1 wherein the amount of particulate matter added is between 1 to 2 pounds per 1000 pounds of materials that are to be blend.

8. A method of monitoring and evaluating the dry-blending of powders and granular materials according to claim 1 wherein the particulate matter is mustard seed.

9. A method of monitoring and evaluating the blending of materials comprising:
   a. adding a known amount of non-dissolvable particulate matter to a known amount of materials that are to be blend in a mixture,
   b. blending the mixture for a time interval,
   c. taking a known amount of sample from the mixture,
   d. separating the particulate matter from the other materials in the
   sample,
   e. determining the amount of particulate matter in the sample either by weighing the particulate matter or by counting the particulate matter, and
   f. comparing the actual amount of particulate matter found in the sample verses the expected amount of particulate matter in a completely mixed blend to determine whether the mixture is completely mixed.

10. A method of monitoring and evaluating the blending of materials according to claim 9 further comprising:
    g. repeating steps b-f until the determined amount of particulate matter in the sample is the same as the expected amount of particulate matter in a completely mixed blend which indicates that the mixture is completely mixed.

11. A method of monitoring and evaluating the blending of materials according to claim 9 wherein the particulate matter is separated from the other materials in the sample by sieving the particulate matter through a mesh screen sieve.

12. A method of monitoring and evaluating the blending of materials according to claim 11 wherein the wire mesh screen is selected from the following list:
    20 mesh screen sieve and 30 mesh screen sieve.

13. A method of monitoring and evaluating the blending of materials according to claim 9 wherein the sample is weighted before the particulate matter is separated from the sample and the particulate matter is weighed after it is separated from the sample to determine the amount of particulate matter in the sample.

14. A method of monitoring and evaluating the blending of materials according to claim 9 wherein a known volume of sample is used and the particulate matter that is separated from the sample is counted to determine the amount of particulate matter in the sample.

15. A method of monitoring and evaluating the blending of materials according to claim 9 wherein the amount of particulate matter added is between 1 to 2 pounds per 1000 pounds of materials that are to be blend.

16. A method of monitoring and evaluating the blending of materials according to claim 9 wherein the particulate matter is mustard seed.

* * * * *